(12) United States Patent
Dufour et al.

(10) Patent No.: US 12,399,969 B2
(45) Date of Patent: Aug. 26, 2025

(54) COMPUTER-IMPLEMENTED METHOD OF PERFORMING A COMPARISON BETWEEN AN ACTUAL RESPONSE TO IMAGE STIMULI AND A RESPONSE TEMPLATE

(71) Applicant: INSTITUT NATIONAL D'OPTIQUE, Québec (CA)

(72) Inventors: Suzie Dufour, Québec (CA); Pierre Galarneau, Québec (CA); André Fougeres, Québec (CA)

(73) Assignee: INSTITUT NATIONAL D'OPTIQUE, Quebec (CA)

( * ) Notice: Subject to any disclaimer, the term of this patent is extended or adjusted under 35 U.S.C. 154(b) by 341 days.

(21) Appl. No.: 18/191,997

(22) Filed: Mar. 29, 2023

(65) Prior Publication Data

US 2023/0315825 A1 Oct. 5, 2023

Related U.S. Application Data

(60) Provisional application No. 63/325,869, filed on Mar. 31, 2022.

(51) Int. Cl.
*G06F 21/32* (2013.01)
*A61B 5/024* (2006.01)
(Continued)

(52) U.S. Cl.
CPC .......... *G06F 21/32* (2013.01); *A61B 5/02405* (2013.01); *A61B 5/0816* (2013.01);
(Continued)

(58) Field of Classification Search
CPC ...... G06F 21/32; G06V 40/174; G06V 10/56; G06V 10/761; G06V 40/193; A61B 5/02405; A61B 5/0816
See application file for complete search history.

(56) References Cited

U.S. PATENT DOCUMENTS

| 5,325,862 A | 7/1994 | Lewis et al. |
| 7,249,263 B2 | 7/2007 | Chaudhari et al. |
| (Continued) | | |

OTHER PUBLICATIONS

Azizi et al., Authentication with brainwaves : a review on the application of EEG as an authentication method, IEEE Xplore, 2018.

*Primary Examiner* — Wassim Mahrouka
(74) *Attorney, Agent, or Firm* — Alexandre Daoust; Norton Rose Fulbright Canada LLP

(57) ABSTRACT

The method can include acquiring response data including a digital representation of an actual physiological reflex response of a user to exposure to a stimuli sequence associated to the user ID, the stimuli sequence including personal images and generic images; providing response template data associated to the user ID, the response template data including a digital representation of a baseline physiological reflex response of a user corresponding to the user ID to exposure to the stimuli sequence; computing a normalization parameter based on a comparison between the response data associated to the generic images and the response template data associated to the generic images, and comparing the response data associated to the personal images to the response template data associated to the personal images, including factoring out a noise component based on the normalization parameter.

7 Claims, 9 Drawing Sheets

(51) Int. Cl.
*A61B 5/08* (2006.01)
*G06V 10/56* (2022.01)
*G06V 10/74* (2022.01)
*G06V 40/16* (2022.01)
*G06V 40/18* (2022.01)

(52) U.S. Cl.
CPC ............ *G06V 10/56* (2022.01); *G06V 10/761* (2022.01); *G06V 40/174* (2022.01); *G06V 40/193* (2022.01)

(56) References Cited

U.S. PATENT DOCUMENTS

| | | | |
|---|---|---|---|
| 9,477,823 B1* | 10/2016 | Ott | G06F 21/316 |
| 9,886,493 B2 | 2/2018 | Coleman et al. | |
| 10,617,351 B2 | 4/2020 | Rau et al. | |
| 11,507,924 B1* | 11/2022 | Kocher | A61B 5/0057 |
| 2005/0022034 A1* | 1/2005 | Chaudhari | G06F 21/32 |
| | | | 726/19 |
| 2008/0234601 A1 | 9/2008 | Wexelman | |
| 2014/0020089 A1 | 1/2014 | Perini, II | |
| 2014/0315168 A1 | 10/2014 | Movellan et al. | |
| 2017/0103885 A1 | 4/2017 | Nakamura | |
| 2019/0239791 A1 | 8/2019 | Beck et al. | |
| 2020/0257787 A1* | 8/2020 | Eyole | A61B 5/117 |

\* cited by examiner

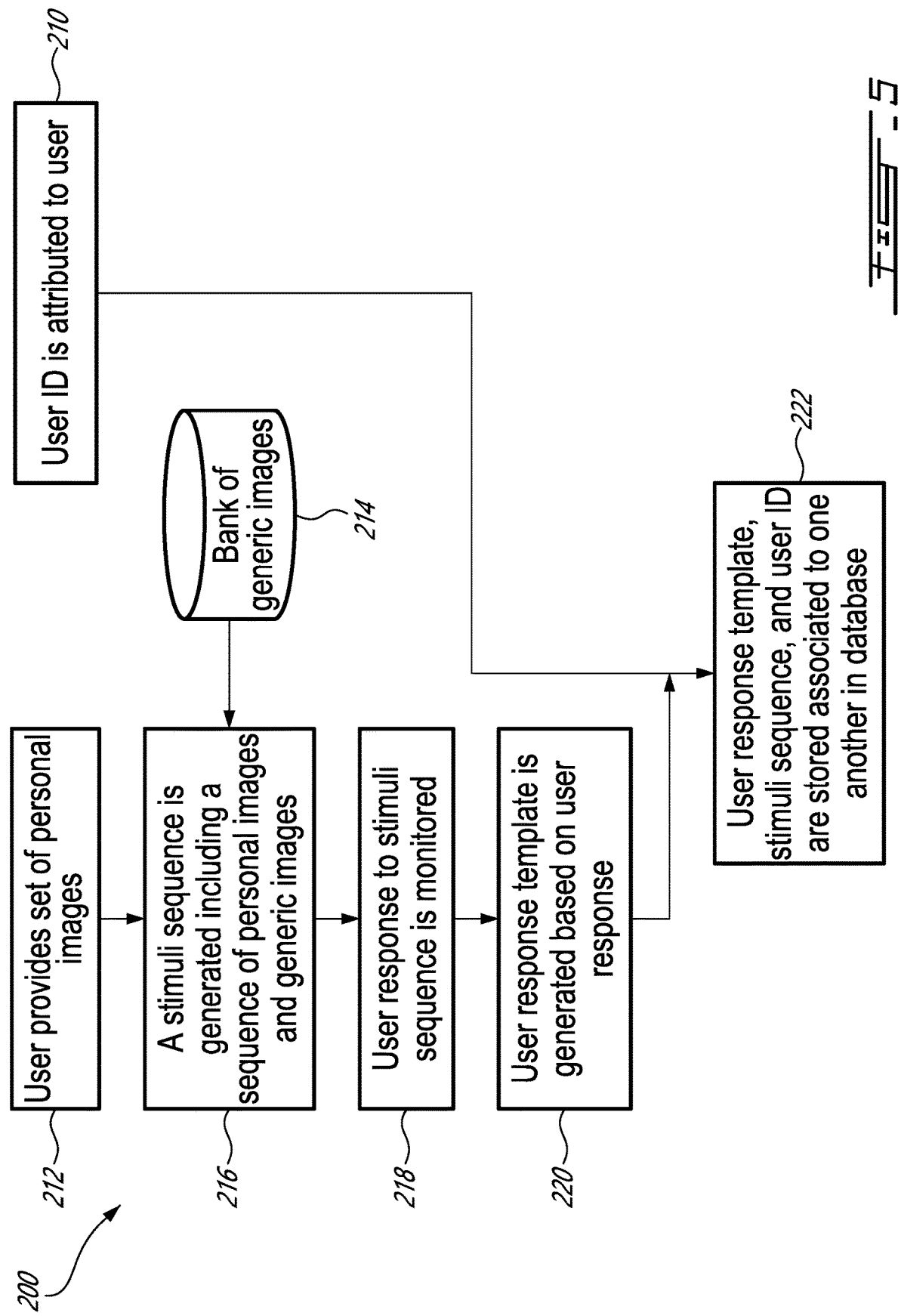

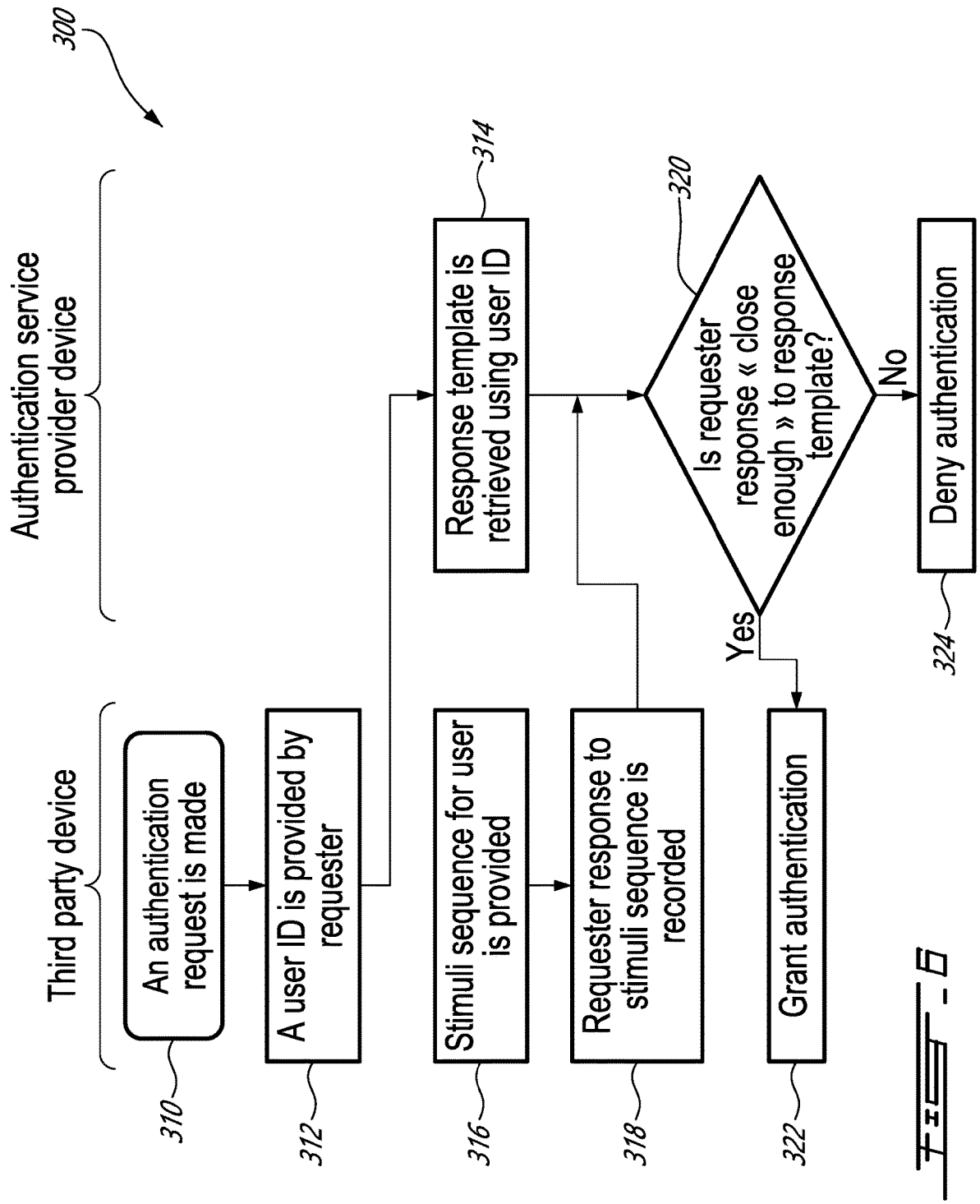

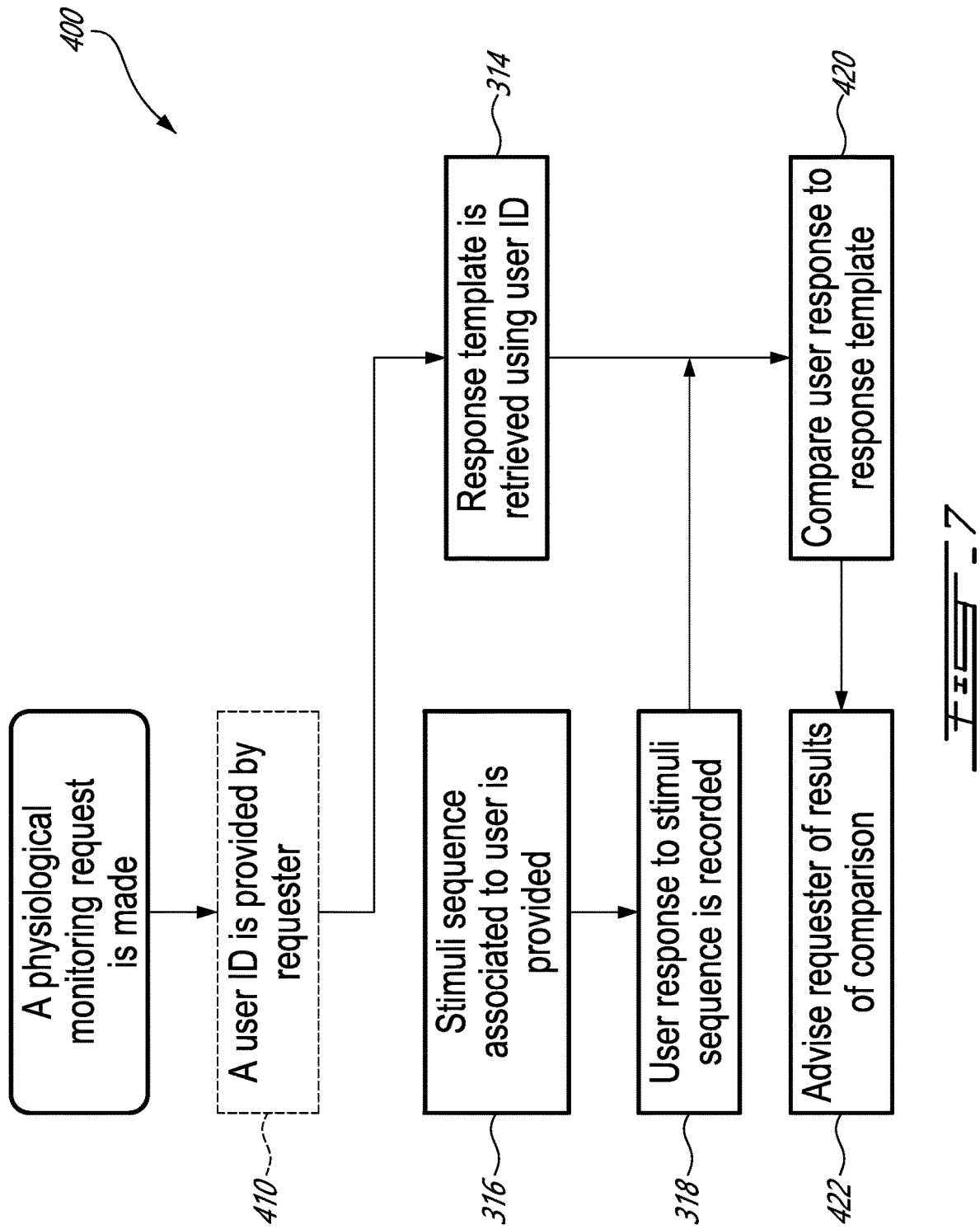

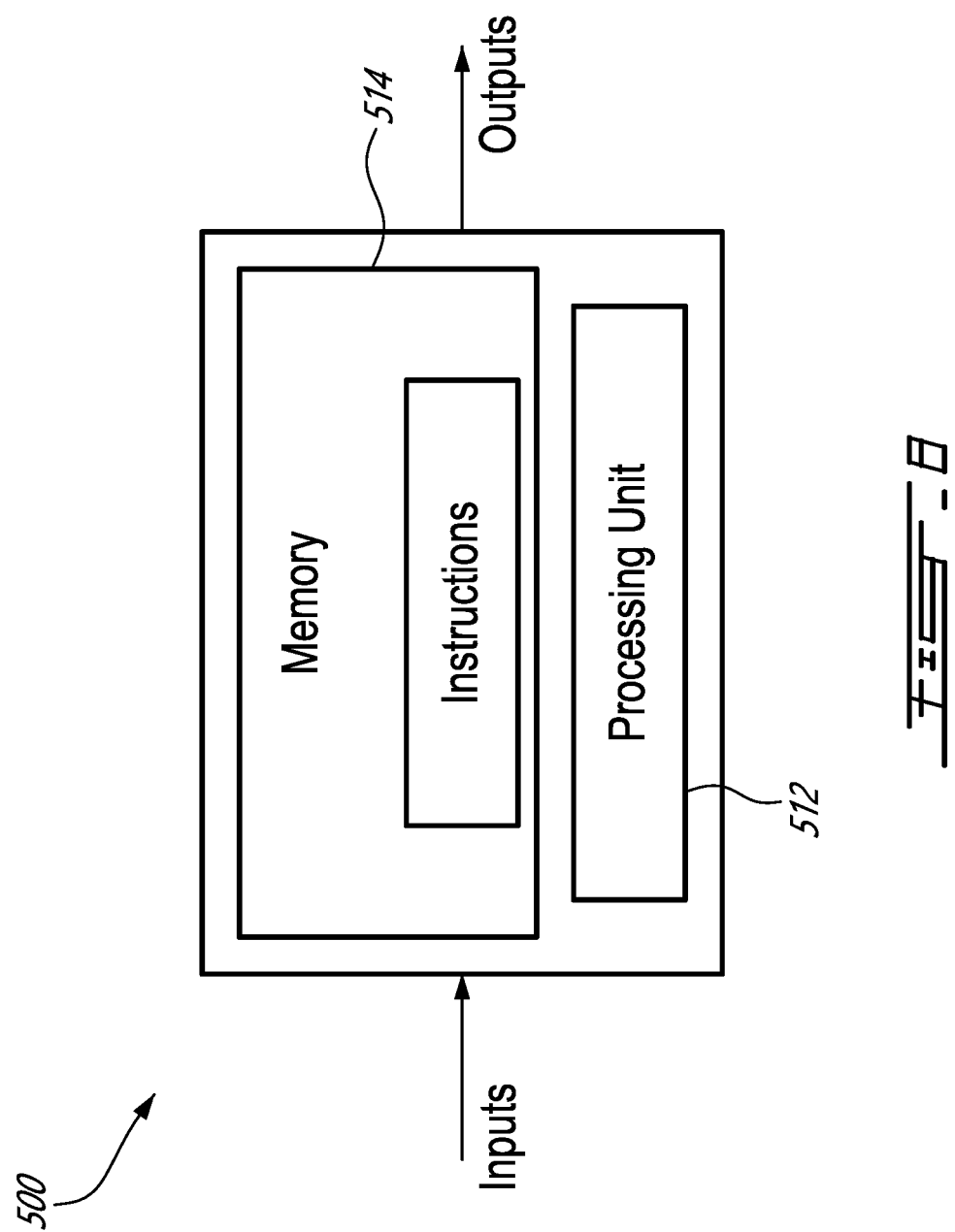

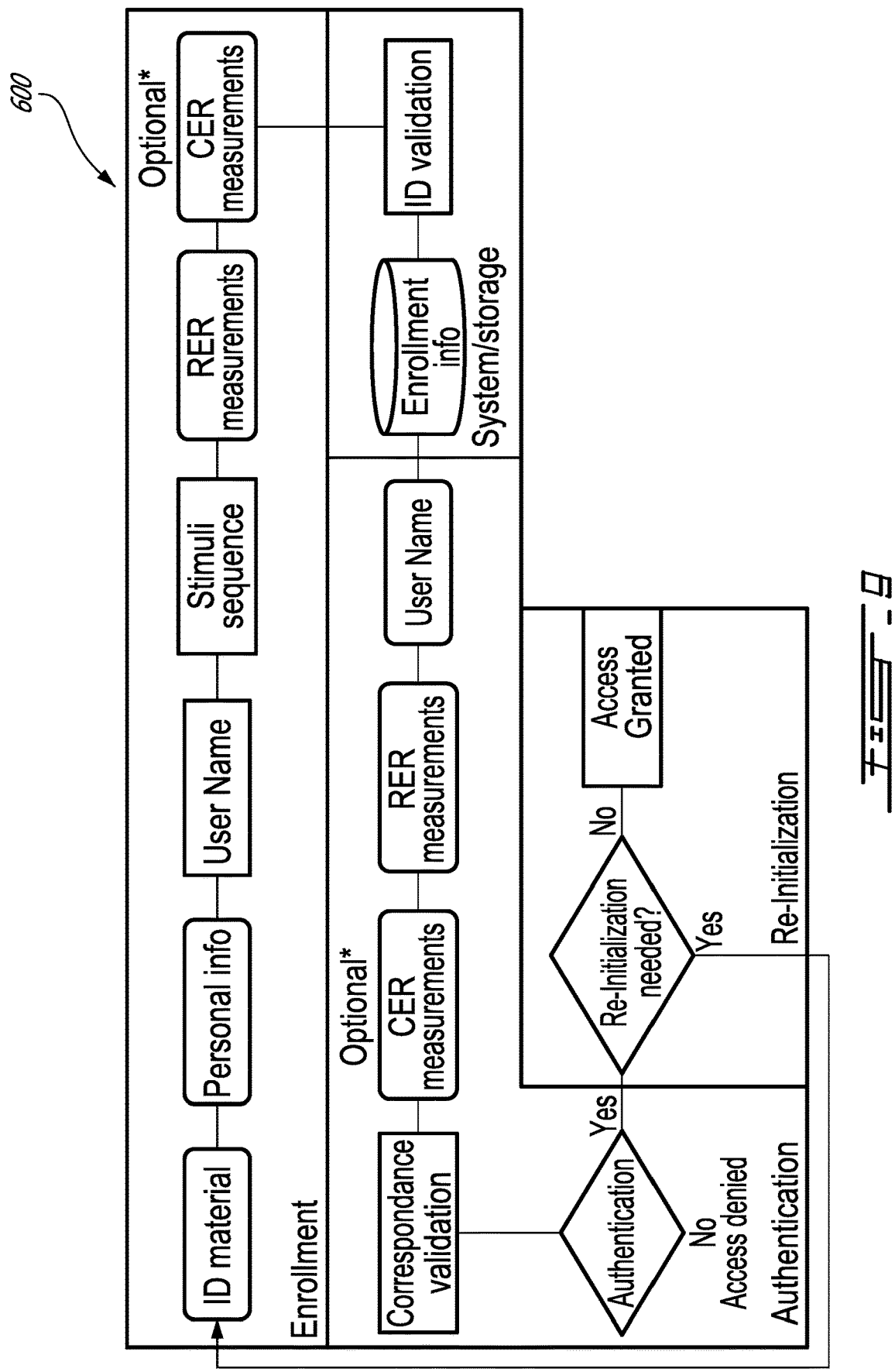

COMPUTER-IMPLEMENTED METHOD OF PERFORMING A COMPARISON BETWEEN AN ACTUAL RESPONSE TO IMAGE STIMULI AND A RESPONSE TEMPLATE

BACKGROUND

Reflex responses to sensory stimuli can include, in some instances, a physiological signature which is specific to an individual and can thus be used for biometry. While similarities in cognitive responses may be shared amongst different individuals, the reflex responses from the central nervous system, including the sensory cortex response, can vary between individuals and contain an individual physiological signature. Indeed, following sensory stimuli, a measured physiological response can include both a reflex response component and a cognitive response component. By contrast with cognitive responses, reflex responses typically occur within a timeframe shorter than a minimum timeframe which would allow conscious interference.

As such, reflex responses have raised interest in the field of secure authentication, for instance. However, commercial uses have been limited. Indeed, there can be various challenges. For instance, there can be a challenge associated with acquiring a biometric signature stemming from a reflex response (e.g. costs or availability of associated acquisition and/or stimuli-exposure equipment). There can be a challenge associated to managing the volume of data associated to the response. There can be a challenge associated with achieving a comparison within a sufficient degree of precision, or other challenges. Accordingly, there remains room for improvement yet.

SUMMARY

While an individual may consciously alter his/her cognitive response to a stimulus, the reflex response is not as easily altered and is a candidate for a unique and constant biometric signature. In both cases, the responses are generated by the central nervous system whose transfer function is unknown to the individual being stimulated, and as such, the responses are highly non-communicable from person to person.

It was found that using a sequence of images as a source of reflex response stimulation could be interesting from the point of view of non-invasiveness and practicality (e.g. display screens and related devices, such as smartphones, are ubiquitous). Such a sequence of images can be displayed at a subliminal rhythm (e.g. below the 10's of millisecond range), faster than the timeframe allowing a person to consciously react to the images. Moreover, using this type of stimuli in an authentication context, in particular, can be interesting from the point of view of re-initialization. Indeed, typically, biometric authentication methods are not re-initializable, whereas a reflex response to a sequence of images can be reinitialized simply by changing the sequence of images. Via an initialization step, for instance, a response template can be generated for a user including recording the user's reflex response to the images. Later, a subsequent reflex response to the same images can be acquired and compared to the response template. In the context of authentication, for instance, authentication can be granted if the subsequent reflex response matches the response template sufficiently closely.

Such a method may have interest outside the context of authentication. For instance, such a method may be used in a context of health-related monitoring such as determining if the reflex response of a person has changed over time. Indeed, a change of the reflex response over time may be caused by aging, disease, and/or alcohol or drug use, for instance. Such a method can be based on determining whether the reflex response matches or mismatches the response template to a certain degree, which can be defined in the form of one or more threshold values associated to a degree of similarity or dissimilarity, for instance. Indeed, the related questions of establishing a sufficiently close match or sufficiently distinct mismatch between a response and a template can be similar from the point of view of hardware and software implementation. Moreover, in some embodiments, rather than quantifying a degree of matching (or mismatching) and comparing such a value to a threshold to yield a binary result, it may be preferred to simply quantify the degree of similarity (or dissimilarity) and to output that value as a result.

Notwithstanding the apparent interest in using a sequence of images as a source of reflex response, as evoked above, there can be practical challenges to achieve widespread, commercial use. In particular, one challenge may be related to making the basis of the comparison sufficiently narrow to achieve sufficient discrimination between, say, different individuals, while making the basis of the comparison sufficiently broad to avoid issues which may otherwise be associated with false outcomes. In other words, there can be a challenge in satisfactorily avoiding both false negatives and false positives in the context of a specific application.

In particular, a reflex response can be affected by factors other than the stimuli. For example, a reflex response may be acquired by monitoring changes in a measurable parameter such as a parameter indicative of minute changes in facial expression or skin color (which can be affected by blood circulation), such as by measuring changes in images or in a video of the user acquired with a camera. However, environmental or non-targeted physiological changes between the initialization context and the comparison context may affect the perceptibility of the changes. Such environmental or non-targeted physiological changes can stem, for instance, from the presence of uncontrolled external stimuli that do not relate at all to the sequence of image stimuli (e.g. the person gets distracted by a surrounding event), from changes in lighting, or other ambient condition of use, and/or from fatigue or a hormonal basal level variation to name a few possible examples. Such environmental or non-targeted physiological changes can be referred to as generic deviations and considered as a source of "noise" in the context, as they may not be relevant to the function of monitoring the evolution or stability of a targeted physiological change. The presence of such potential variations can motivate the broadening of the basis of comparison to avoid concluding that a change in the reflex response of the person has occurred when, in fact, the detected change is caused not by the reflex response, but by the external changes in environmental and/or non-targeted physiological conditions (i.e. to account for the potential presence of noise as defined above). However, broadening the basis of comparison (e.g. by requiring for instance a 95% match probability instead of a 99% match probability) in such a way can also open the door to falsely concluding that no change is present, when a change of a nature intended to be detected is indeed present between the subsequent response and the response template, and may thus not be fully satisfactory in some embodiments.

It was found that such challenges could be addressed, at least in some embodiments, by a technique allowing to factor out at least some of such generic deviations. Such a technique can involve, for instance, introducing two (or more) different types of images in the sequence of images, such as personal images which may be known to generate a more pronounced or more unique reflex response (such as when associated to profound emotional souvenirs specific to the individual), and generic images. The reflex response data and the response template data can be coded in a manner that specific portions of the reflex response can be associated to specific ones of the images. Accordingly, the reflex response data associated to the generic images can be compared to the response template data associated to those generic images, and a normalization parameter may be computed based on this latter comparison. The normalization parameter can alternately be referred to as a noise parameter in a context where the generic deviations may be considered to be a source of noise in a comparison which would include generic deviations in addition to a reflex response. A noise component in the reflex response data associated to the personal images can then be factored out based on the noise parameter. Stated otherwise, the comparison can be performed in a normalized state. For instance, the reflex response data associated to the personal images can be compared to the response template data associated to the personal images, at which stage the generic deviations can be factored out from the response data by normalizing one to the other, based on the normalization parameter. Accordingly, the basis of the comparison between the "generic deviation-removed" (e.g. normalized) reflex response data and the response template data can be made tighter due to the removal of the generic deviations (e.g. by requiring a 99% match probability in the normalized condition), leaving a normalized comparison result more specifically indicative of any changes in the targeted reflex response as opposed to any changes which would be due to generic deviations, or "noise".

In accordance with one aspect, there is provided a computer-implemented method comprising: acquiring a user ID; acquiring response data including a digital representation of an actual physiological reflex response of a human to exposure to a stimuli sequence associated to the user ID, the stimuli sequence including a sequence of images, the images including personal images and generic images, the personal images being personal to the user ID, the response data including response data associated to the personal images and response data associated to the generic images; providing response template data associated to the user ID, the response template data including a digital representation of a baseline physiological reflex response of a user corresponding to the user ID to exposure to the stimuli sequence, the response template data including response template data associated to the personal images and response template data associated to the generic images; computing a normalization parameter based on a comparison between the response data associated to the generic images and the response template data associated to the generic images; comparing the response data associated to the personal images to the response template data associated to the personal images, including normalizing the response data associated to the personal images to the response template data associated to the personal images based on the normalization parameter; and generating an output based on said comparing the response data associated to the personal images.

In accordance with another aspect, there is provided a computer-implemented method comprising: acquiring a user ID of a user; acquiring a set of personal images from the user; generating a stimuli sequence including a sequence of images, the images including a plurality of said personal images and generic images; acquiring response data including a digital representation of an actual physiological reflex response of the user to exposure to the stimuli sequence, the response data including response data associated to the personal images and response data associated to the generic images; generating response template data based on the acquired response data; and storing the response template data associated with the user ID in a database.

Many further features and combinations thereof concerning the present improvements will appear to those skilled in the art following a reading of the instant disclosure.

DESCRIPTION OF THE FIGURES

In the figures,

FIG. 5 is a flowchart of an example of a computer implemented method for generating a response template for use in a method such as presented in FIG. 1;

FIG. 6 is a flowchart of an example method of authentication;

FIG. 7 is a flowchart of an example method of physiological monitoring;

FIG. 8 is a block diagram of a computer; and

FIG. 9 is a flowchart of a detailed example of an authentication-related embodiment.

DETAILED DESCRIPTION

Figure 1:
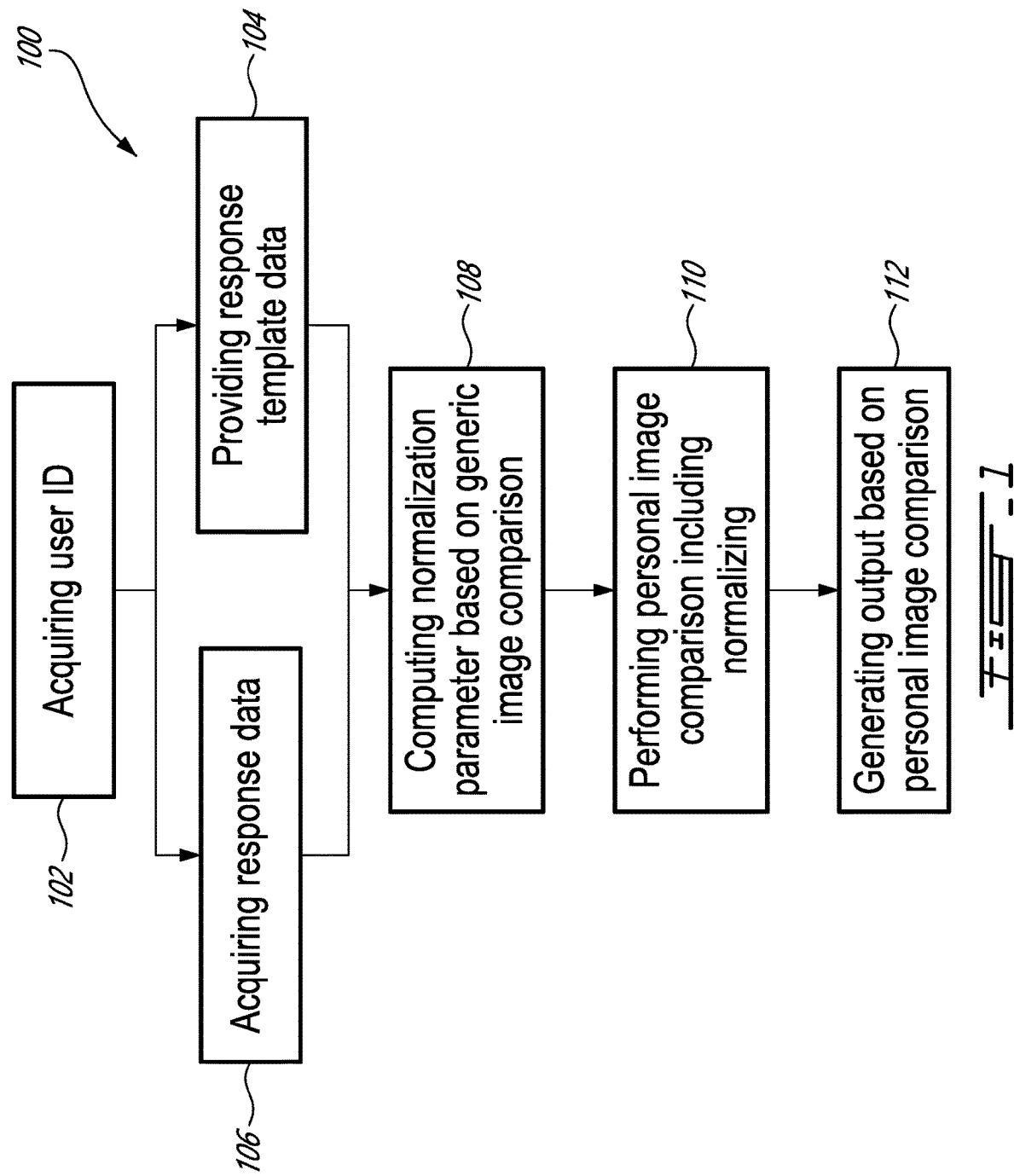
FIG. 1 is a flowchart of an example of a computer implemented method of performing a comparison between response data and response template data in a normalized state.

FIG. 1 shows a flowchart of an example of a method 100 which involves performing a comparison between an actual physiological response and a response template in a normalized state. The method 100 is computer implemented and the computer operates on data items which are indicative of physiological responses. More specifically, the actual physiological response is encoded in response data while the response template is encoded in response template data. In most practical implementations, the method 100 can be enabled for multiple users and, therefore, acquiring 102 a user identification (user ID) of the user concerned by a given instance of the method can be useful. The user ID can be provided as an input to a computer or software application, for instance. For example, the user ID can be used as a key to retrieve the response template associated to the user ID from a database. In this example, the response template is acquired 104 before executing the method 100 presented in FIG. 1, at a stage which can be referred to as "initialization", an example of which will be presented below with reference to FIG. 2.

Returning to FIG. 1, in step 106 response data including a digital representation of an actual physiological reflex response of a human to exposure to a stimuli sequence is also acquired. In practice, the response data can be acquired by exposing the human to a stimuli sequence which is associated to the user ID, and may involve retrieving the corresponding stimuli sequence from a database using the user ID as a key. The stimuli sequence can consist of a sequence of images, including both "personal" images and generic images. The personal images can have been previously provided by or selected by a user on the basis of representing something meaningful/personal to the user, or otherwise stimulate a distinctive reflex response when displayed to that specific user. The generic images can be non-personal to the user, such as by being selected randomly from a bank of images for instance, and may thus not be expected to stimulate a distinctive reflex response when displayed to the user. Acquiring 106 the response data can involve exposing the human to the stimuli sequence while monitoring the physiological reflex response of that human and converting it into digital response data. The displaying of the stimuli sequence and the monitoring can be performed by the same electronic device, or by one or more different electronic devices. According to the features and capabilities of the electronic device performing the method of FIG. 1, these steps can be abstracted and simplified to acquiring 106 response data, which may or may not include the actual control of the displaying and monitoring steps.

The response template data and the response data can be encoded on a common framework allowing to associate corresponding portions of the response or response template to corresponding ones of the images of the stimuli sequence. A relatively simple example of a common framework can be a common timeline to both the response, the response template, and to the stimuli sequence, but more elaborate frameworks are possible as well.

Figure 2:
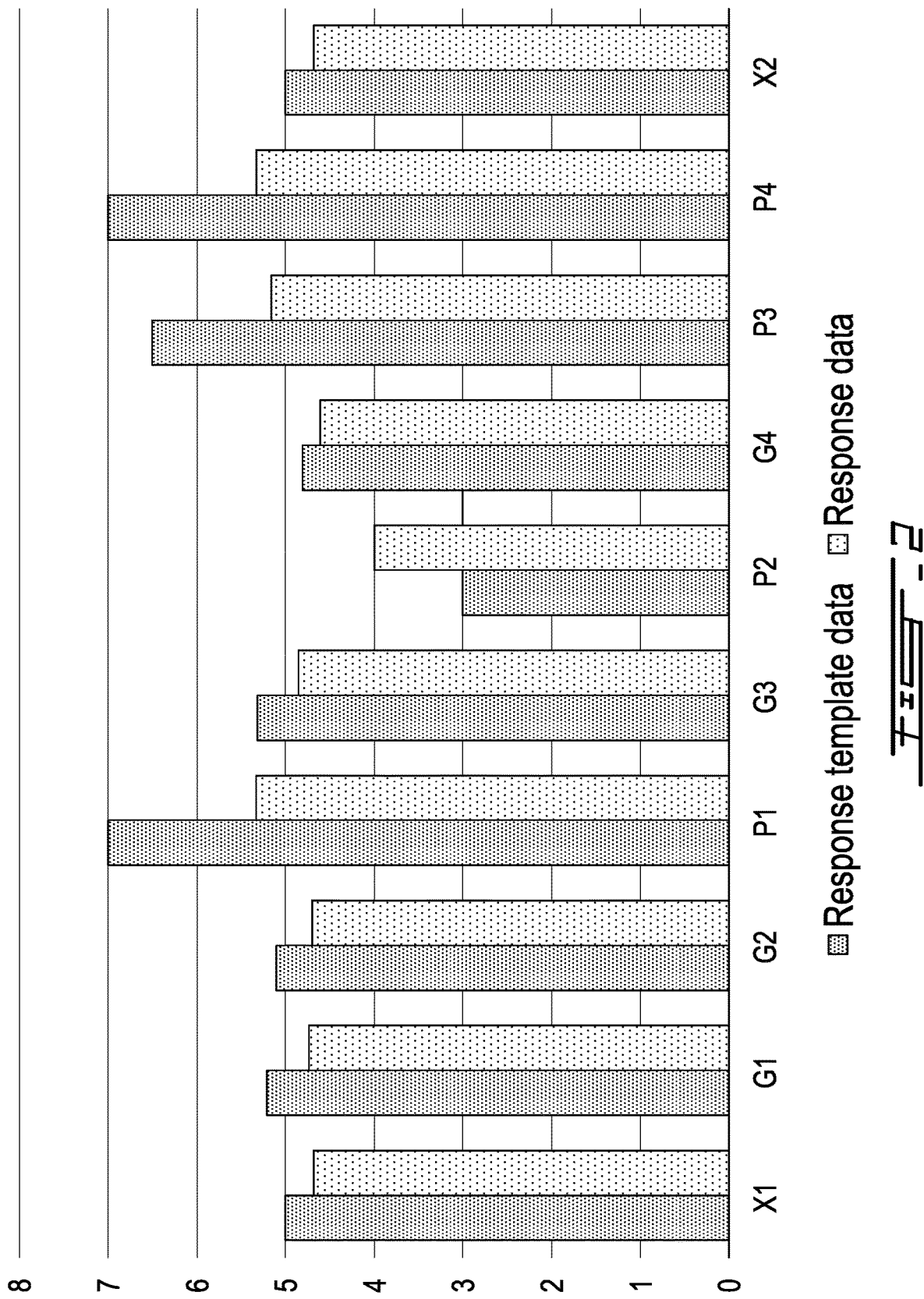
FIG. 2 is a graph showing an example of response template data and of response data for a given sequence of image stimuli.

An example of response template data and of response data encoded on a common timeline is presented in FIG. 2. In this schematic example, the value of an arbitrary parameter (e.g. a single measured parameter or of a composite value stemming from measurements of different parameters) is plotted for a plurality of pairs of timeslots of the common timeline. Each pair of timeslots has a response timeslot bearing a value of the response data associated to a given image of the stimuli sequence, and a response template timeslot bearing a value of the response template data associated to that same image of the stimuli sequence. Here, G1, G2, G3 and G4 are values of a parameter corresponding to portions of the stimuli sequence where corresponding generic images are displayed (referred to below as generic timeslots). Likewise, P1, P2, P3 and P4 are values of the parameter corresponding to portions of the stimuli sequence where corresponding personal images are displayed (referred to below as personal timeslots). In this example, values of the parameter are present at two additional timeslots, identified as X1 and X2 on the horizontal axis of the graph, and those timeslots correspond to periods of time during which the user response is recorded while no image is being presented. Such timeslots are optional, but it may nonetheless be desired to use them in some embodiments. Such timeslots may be present and then ignored when determining the normalization parameter or performing the comparison, or may be present and contribute to determining the normalization parameter, for instance. Although shown here side by side, it will be understood that the baseline physiological reflex response present in the response template data will typically have been acquired at an earlier moment than the actual physiological reflex response present in the response data. The values of the response template data can stem from a single prior acquisition performed with the same user, or can be based on a plurality of prior acquisitions, such as by being average values or median values associated to a plurality of measured values. Moreover, while response timeslots are paired with response template timeslots associated to a same image in the common timeline of FIG. 2, the corresponding values may have been acquired via exposure of images in a different order in the response data than in the response template data.

Referring back to FIG. 1, when the response data and the response template data are both available, a normalization parameter, or noise parameter, can be computed at step 108. The normalization parameter can be computed based on a comparison between the portions of the response data associated to the generic images of the stimuli sequence, and the corresponding portions of the response template data also associated to the generic images.

Figure 3:
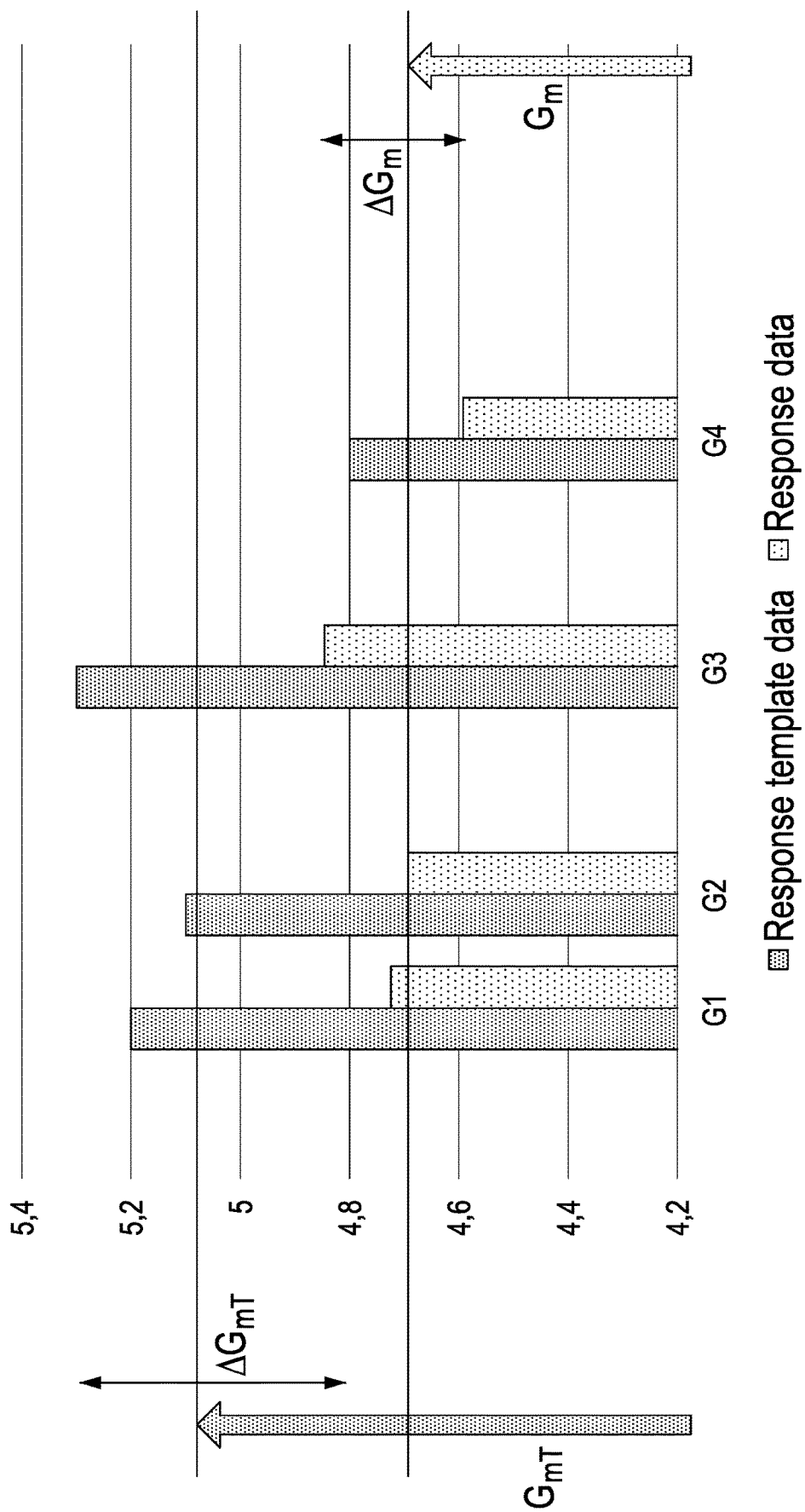
FIG. 3 schematizes the determination of a normalization parameter.

FIG. 3 presents an example of how such a normalization parameter can be computed, in one embodiment. The comparison involves the values associated to the generic timeslots in the response data and values associated to the generic timeslots in the response template data. More specifically, the method can include determining an average value $G_m$ of the values of the measured parameter associated to the generic timeslots in the response data, and determining an average value $G_{mT}$ of the values of the measured parameter associated to the generic timeslots in the response template data. In this specific example, the method can further include determining a variability $\Delta G_m$ of these values in the response data relative their average value $G_m$, and determining a variability $\Delta G_{mT}$ of these values in the response template data relative their average value $G_{mT}$. Those values can then be used to normalize the overall data set (e.g. to remove a noise component) and the normalized responses can be used to evaluate the degree of similarity between the response data and the response template data.

Referring back to FIG. 1, in step 110 the personal image comparison may then be performed including a normalization. More specifically, the values of the response data associated to the personal images can be normalized to the values of the response template data based on the normalization parameter. In other words, a generic deviation component associated with the portions of the response data and/or response template data associated to the personal images can be factored out using the normalization parameter, allowing to perform a comparison between the values of the measured parameter associated to the personal timeslots in the response data and the corresponding values in the response template data which, in principle, would be expected to more closely correlate once the generic deviation component associated with external factors (noise component) has been factored out. The presence of a significant difference in this comparison can be more reliably associated to a difference between a targeted physiological state of the person being monitored and a template, or baseline state, and less likely to have been affected by other factors such as a difference between a non-targeted physiological state and a baseline state or environmental factors such as lighting or the presence of a distraction in the acquisition environment.

Figure 4:
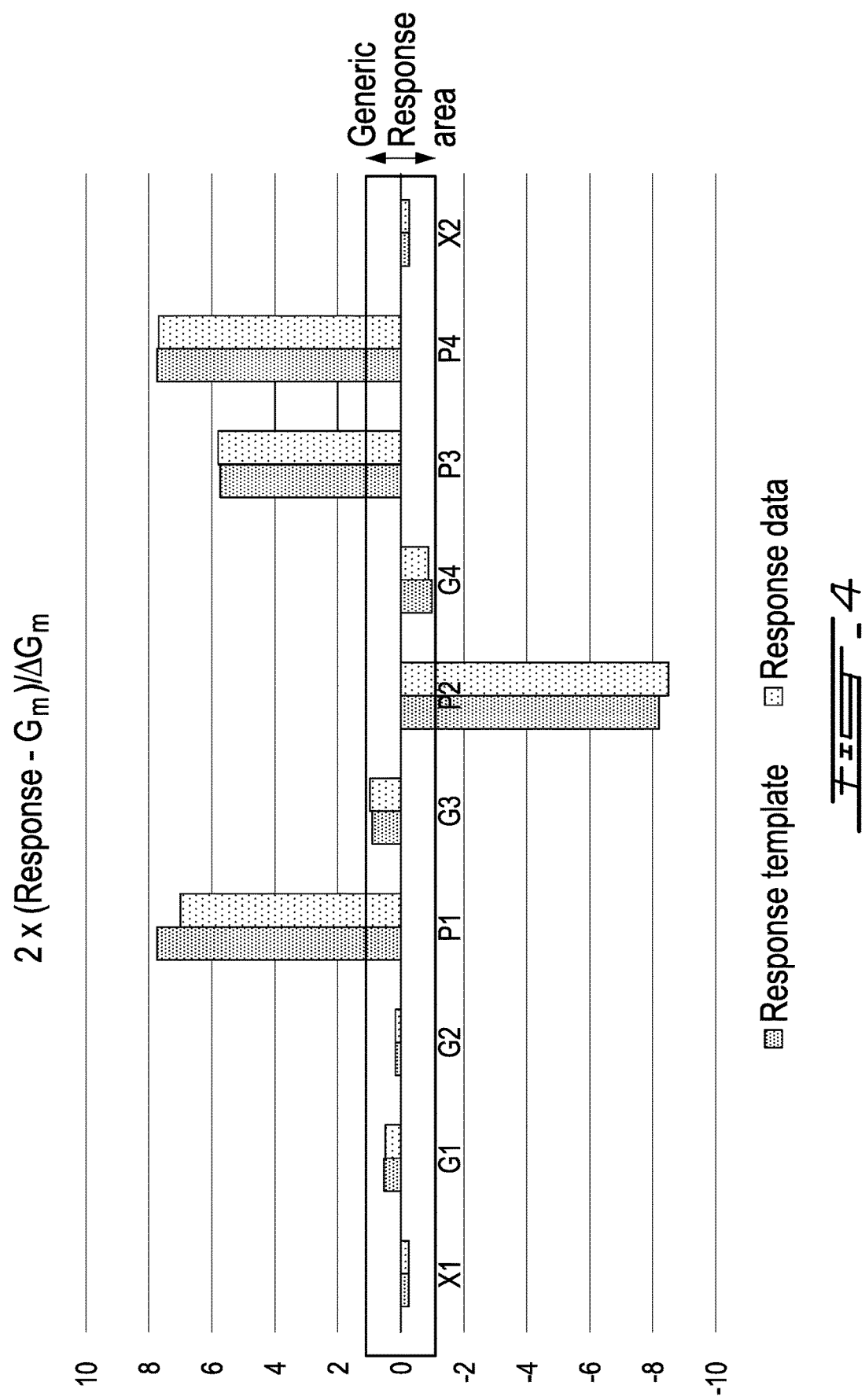
FIG. 4 schematizes the comparison of response template data to response data in the normalized state.

Using the simplistic example evoked above and a simple linear normalization factor, the response data can be compared to the corresponding response template data by subtracting the average value of the generic response and dividing by half the possible variation of the response. Using such an example normalization step, all responses between 1 and −1 are within the generic response area, and differences of this scale may be classified as noise. Responses over ±1 are considered to include a personal reflex response to the stimuli, and the larger the number, the more intense the personal response with respect to generic response amplitude and the higher the confidence level or degree of similarity. FIG. 4 shows such an example and the correspondence between the response data and the response template data on the basis of the data presented in FIGS. 2 and 3. Accordingly, a method including the removal from the basis of the comparison of slots P1-P4 (i.e. the comparison of the response data to the response template data for each slot) in FIG. 3 any difference which is considered to be associated to the normalization parameter (e.g. differences within ±1 in this example) can be considered a normalized comparison in which the noise component has been factored out.

Referring back to FIG. 1, the comparison 110 between the response data and the response template data can then be made in the normalized state. The normalized state can constitute a better framework for extracting significance from the comparison. In this example, one may wish to measure a difference between the response data and the response template data associated to the personal images in the stimuli sequence. The measured difference can be directly outputted, or, in some embodiments, compared to a threshold value to yield a binary result, such as authenticated/non-authenticated, no disease/disease, intoxicated/non-intoxicated, etc.

In the example illustrated in FIG. 4, there are four values of a parameter being compared to four corresponding values of the response template at P1, P2, P3 and P4. One example of determining a difference between the response data associated to the personal images normalized to the corresponding response template data can be to calculate the difference between each measured value and the corresponding template value, and to use the sum or an average of the differences as a result of the comparison. In a somewhat more elaborate example, outliers may be removed prior to performing the comparison. In still other example embodiments, weighted comparison techniques where different values are given different relative weights in the comparison may also be used.

For the purpose of illustration, let us take a simple example of an embodiment where a single value, say a value of heart rate, is being compared. In the response template data, the heart rate at rest is 65 (beats per minute), while in the response data the heart rate at rest is 80. Fluctuations of the heart rate may be monitored to above and/or below 80 when the person is subjected to the personal images in the stimuli sequence. Similarly, the fluctuations of the heart rate may have similarly varied to above and/or below 65 in the corresponding timeslots of the response template data. The fluctuations in the response data can then be normalized to the fluctuations in the response template data so as to take the variations between the base heart rates, 65 vs 80, out of the basis of the comparison. Here, the departures from 80 in the response template data can now be compared to the departures from 65 in the response template data, and the differences between the departures can serve as a basis of the comparison, in a context where there is an overarching difference, representing a source of generic deviation, in the basic heart rate between the conditions at which the response template data was acquired and the conditions at which the response data is acquired. Here, specific fluctuations from that basic heart rate can provide an indication of a reflex response better than the absolute value of the heart rate. Accordingly, the comparison in the normalized state is performed between departures from 80 and departures from 65.

Referring back to FIG. 1, in step 112 an output based on the response to personal image comparison can be generated. In the context of an authentication method, the output can direct the authentication or non-authentication of the human person being monitored as being indeed the user, for instance. In the context of a physiological monitoring method, the output can be in the form of a degree of similarity or departure, which may be used to inform a person (e.g. patient, athlete, worker) being monitored, or a healthcare professional associated to that person. For instance, a value of a degree of similarity or of departure may provide an indicator that the patient's physiological state has evolved relative to a given reference/baseline state, together with an indication of the extent by which the state has evolved. More specifically, and depending on the application, it may be desired to target a particular physiological parameter such as alertness, or a physiological parameter associated to a particular disease (e.g. patients suffering from schizophrenia may be expected to react differently to Rorschach-type images than patients not suffering from schizophrenia). Both these scenarios will be explored below, but we will begin by looking into an example of how initialization can be performed.

It will be noted that although in the simplistic example presented in relation with FIGS. 2 to 4 the order of the sequence of the different portions is the same between the response data and the response template data, in an alternate example, the sequence can be different. Indeed, as long as the difference in order is known and that portions of the response data can be compared to corresponding portions of the response template data (portions corresponding to corresponding images), there can be embodiments where the order may be different. If the order is different, a key identifying the order may be provided. In one embodiment, the key identifying the correct order may be the same from one instance of the method to another, whereas in another embodiment the key identifying the correct order may be randomly generated or otherwise change from one instance of the method to another, i.e. as an additional security measure.

FIG. 5 presents an example of an initialization method 200, or otherwise said, a method of creating the response template data. The method may be a first initialization or, if required for a reason or another, a re-initialization subsequent to a first initialization. The method can involve feature extraction and storage, for instance. Initial steps in this method can include the attribution 210 of a user ID to the individual for which the initialisation method is being performed (user), and providing a selection of personal images. The user ID can take various forms, but it can be practical in many embodiments for the user ID to include a relatively short, and characteristic/unique, string of alphabetical, symbol, and/or numerical, characters for instance. The user ID can be selected or entered by the user, alternately be provided by a service provider of the method, for instance. The user ID can be used subsequently for various reasons, such as retrieving the response template associated to a given user and also for retrieving a stimuli sequence associated to a given user, for instance. The personal images can be provided by the user, or selected by the user from a proposed image library for instance (both cases will be referred to herein as "provided 212 by the user" for simplicity). As presented above, the personal images can be personal to the user in the sense that they evoke a distinctive reflex response in that user which would not be likely to be evoked similarly in other humans not reflexively/emotionally linked to the personal images in the same manner. For instance, the personal images can be a selection of images taken from the user's personal image library, such as pictures taken by the user him/herself, or images taken by persons close to the user and representing events or people with whom the user has a special emotional attachment. In another instance, the personal images can be selected by a user on the basis of generating a significant emotional response. In the context of re-initialization, care can be taken to avoid using the same set of personal images that was used in the previous initialization step.

Then, the stimuli sequence is generated 216. The stimuli sequence can include a sequence of images including both some or all of the personal images, and generic images. The generic images can be randomly selected from a bank of generic images 214 in an automated manner, for instance. In one embodiment, the personal images will be specific to the stimuli sequence of the unique user ID associated to the user, whereas the generic images can be used in the stimuli sequences of a plurality of user IDs.

Then, the user is exposed to the stimuli sequence, and the actual physiological reflex response of the user to the stimuli sequence is monitored 218 during the exposure. Depending on the embodiment, the nature of the actual physiological reflex response can vary. For instance, the actual physiological reflex response measurement or monitoring can involve non-invasive techniques, such as being based on one or more of minute changes in facial expression, eye movements, iris dilation, respiratory rate changes, heart rate changes, or changes in skin color for instance, or involve somewhat more invasive techniques such as acquiring an electroencephalogram (EEG), electrocardiogram (ECG), electromyogram (EMG), magnetoencephalogram (MEG), a retinogram (ERG), to name some examples. Various other sources of physiological reflex response monitoring processes may be used depending on the embodiment. In any process of monitoring the physiological reflex response, the resulting data will not provide a perfect or complete representation of the actual physiological reflex response non-intentionally (e.g. because the acquisition hardware has inherent limitations), but also potentially intentionally (e.g. because some form of compression of the acquired data, such as feature extraction for instance, may be deemed relevant in the context). Ultimately, a response template is generated 220 based on the user response, in the form of response template data associated to the user ID, from one or more initial acquisitions of actual physiological reflex responses to the stimuli, to which response data stemming from subsequent acquisitions can be subsequently compared in a suitably reliable manner. The response template data can be formed of response data from an initial acquisition, in raw or compressed form or of an average of response data from more than one initial acquisitions, again in raw or compressed form, to name some examples, and more elaborated techniques can also be used.

Indeed, the response data can be encoded or indexed as a function of references in the stimuli sequence, such as to allow comparing a given point of data in response data of one acquisition to a corresponding point of data in response data of another acquisition, or of the response template for example. For instance, in some embodiments, it can be relevant to extract maxima and minima, or weighted distributions, duration, power spectra, for corresponding images in the stimuli sequence, for a plurality of acquisitions during the initialization process, and to include such references in the response template data. This can form a basis for setting computable thresholds for subsequent comparisons, for instance, where response data resulting from a subsequent acquisition is considered "close enough" to the response template data when all, or a predetermined limited number of the data points are within the minima and maxima for instance, or when a given score based on the weighted distribution is achieved, to name some examples. As such, depending on the embodiment, the response template data can inherently include the basis of comparison with subsequent responses, or the basis of comparison can be set separately from the response template data (e.g. by given maximum, minimum, and/or weighted thresholds, duration, power spectra).

Once the response template data has been generated, it can be stored 222 in a database in association with the user ID, and potentially also in association with the stimuli sequence (e.g. with an identifier of a stimuli sequence), for later retrieval. The response template and the user ID can be stored as part of a same data item in the database, for instance.

The method presented in FIG. 5 can be implemented with one or more electronic devices which can include some form of computer.

For instance, in one embodiment, the acquisition equipment can include one or more user device such as smartphone, a tablet, a laptop or a desktop of the user for instance, either of which may include a computer, a display screen, a communications module, and one or more cameras. In such an embodiment, the stimuli sequence can be displayed on the display screen while the physiological reflex response of the user is monitored by the one or more cameras and/or other monitoring means forming part of the user device. Additional software layers can be overlayed onto such functions if relevant, and simultaneously run on the smartphone hardware, such as to ensure that the user remains within a given range of positions relative to the smartphone or that environmental conditions such as ambient noise and lighting conditions are within certain thresholds, or otherwise allow to validate that the acquisition is performed within predetermined norms. Alternately, the acquisition equipment can exclusively be constituted of service provider equipment.

In an embodiment where the acquisition equipment is a smartphone, tablet or laptop, the same or a different smartphone, tablet or laptop can be used for providing the personal images and/or creating a user ID for instance. Moreover, the same or a different smartphone, tablet or laptop can be used to generate the stimuli sequence, generate the response template, and store the response template in a database (which may be hosted by the user device or on a cloud server for instance), but in some embodiments, especially in methods associated with authentication for instance, it can be preferred that one or more of such latter functions be performed by a separate computer, such as a server associated to the service and/or access provider for instance. The server can be located on premises of the service provider or be a cloud server for instance, and can be enabled to communicate with the smartphone, tablet and/or laptop via a telecommunications network such as the Internet for instance. In particular, in one embodiment, it can be preferred for the initially acquired response data to be communicated directly to the service provider computer and to not be stored in a non-transitory memory of the smartphone, tablet or laptop, as a security measure. In some embodiments, it can be deemed adequate to store the stimuli sequence in non-transitory memory of the user's smartphone, tablet or laptop for instance.

In another embodiment, the initial acquisition step can be performed at service provider premises, using service provider equipment, and potentially in a controlled/secure environment, for instance.

Referring now to FIG. 6, an example method 300 of using the response template and the stimuli sequence as a basis for authentication is presented. In this example method 300, a human who may wish to be authenticated as being the user who had performed an initialization such as presented in FIG. 5, is at the source of an authentication request 310. The human can identify 312 himself by providing a user ID, for instance. The response template associated to the user ID can be retrieved 314 using the user ID. The stimuli sequence is also provided 316 in a manner to allow exposing the human requester to it while monitoring/recording 318 the actual physiological reflex response of the human requester to the stimuli. This subsequent acquisition can be performed in manner similar to that presented above with respect to the one or more initial acquisitions, e.g. involve one or more of a camera, sensor, an electrophysiological acquisition device (e.g. EEG, ECG, ERG, etc.).

The response data acquired by the subsequent acquisition can then be compared 320 to the response template data to determine whether the response data corresponds to the response template data. As presented above with respect to FIGS. 1-4, this comparison process can involve a first step of comparing the portions of the response data and of the response template data which are associated with generic images in the stimuli to compute a normalization parameter, and a subsequent step of factoring out a noise component in the response data associated with the personal images, using the normalization parameter, prior to comparing it to corresponding portions of the response template data. As a result of the comparison, the authentication can be granted 322 or denied 324, for instance, and additional actions or functions, such as triggering a re-initialisation procedure, can also take place.

In the context of an authentication method such as presented in FIG. 6, it may be desired for the human requester to interface with one of his electronic devices, or with an electronic device which is otherwise not an electronic device owned by the authentication service provider. For such reasons, steps such as providing 312 a user ID and recording 318 the response to the stimuli sequence may take place on such a third-party device (e.g. the user's device). It can be desired to avoid sharing the response template with the third-party device, and therefore, the comparison can be hosted on an authentication service provider device (e.g remote server), which can receive the response data from the third-party device via a telecommunications network such as the Internet for instance. Such a scenario may be preferred, in some embodiments, to a scenario where the response template data is provided to the third-party device and the comparison is performed at the third party device. In such scenarios, the stimuli sequence may be hosted in non-transitory memory of the third party device, or may be retrieved with the authentication service provider device based on the user ID and be communicated to the third-party device for temporary use in displaying the stimuli sequence. Alternately, the entire method can be performed by an authentication service provider device, or a computerized device otherwise considered "secure" (e.g. by being located in a secured access environment).

Referring now to FIG. 7, an example method 400 of using the response template and the stimuli sequence response as a basis for a health or alertness monitoring procedure is presented. In this example, the method can be triggered by the user him/herself, or by a healthcare professional for instance, and can take place entirely on a user device or entirely on a healthcare facility device for instance, or different steps of the process may be performed at different computers with data exchange therebetween. In a context where the method 400 needs to retrieve a response template for a given user amongst a plurality of response templates associated to other users, a user ID can be provided by the requester, but if the method is entirely performed on a user device, such as a smartphone for instance, there may be no need for specifically prompting the user to enter a user ID, the user ID can be inherent to the user's device for instance.

In the example method of FIG. 7, the method 400 can have similarities to the method 300 presented in FIG. 6. However, given that the comparison 420 is not performed for the purpose of achieving authentication, the output 422 from the comparison may not need to include a binary output such as authenticate or deny, but rather just provide the requester (e.g. the user or the requesting healthcare professional) with the results of the comparison, which can be in the form of a degree (e.g. % or other suitable numerical, alphabetical or graphical scale) of match between the response data and the response template data. Alternately, one or more given threshold(s) can be set, and corresponding indication(s) can be generated when corresponding threshold(s) are met. Moreover, it may be preferred to engineer the stimuli sequence such as to probe the individual in a specific way (i.e. detection of alertness versus detection of schizophrenia.

Referring to FIG. 8, it will be understood that the expression "computer" 500 as used herein is not to be interpreted in a limiting manner. It is rather used in a broad sense to generally refer to the combination of some form of one or more processing units 512 and some form of memory system 514 accessible by the processing unit(s). The memory system can be of the non-transitory type. The use of the expression "computer" in its singular form as used herein includes within its scope the combination of two or more computers working collaboratively to perform a given function. Moreover, the expression "computer" as used herein includes within its scope the use of partial capabilities of a given processing unit.

A processing unit can be embodied in the form of a general-purpose micro-processor or microcontroller, a digital signal processing (DSP) processor, an integrated circuit, a field programmable gate array (FPGA), a reconfigurable processor or a programmable read-only memory (PROM), to name a few examples.

The memory system can include a suitable combination of any suitable type of computer-readable memory located either internally, externally, and accessible by the processor in a wired or wireless manner, either directly or over a network such as the Internet. A computer-readable memory can be embodied in the form of random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) to name a few examples.

A computer can have one or more input/output (I/O) interface to allow communication with a human user and/or with another computer via an associated input, output, or input/output device such as a keyboard, a mouse, a touchscreen, an antenna, a port, etc. Each I/O interface can enable the computer to communicate and/or exchange data with other components, to access and connect to network resources, to serve applications, and/or perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, Bluetooth, WiMAX), SS7 signaling network, fixed line, local area network, wide area network, to name a few examples.

It will be understood that a computer can perform functions or processes via hardware or a combination of both hardware and software. For example, hardware can include logic gates included as part of a silicon chip of a processor. Software (e.g. application, process) can be in the form of data such as computer-readable instructions stored in a non-transitory computer-readable memory accessible by one or more processing units. With respect to a computer or a processing unit, the expression "configured to" relates to the presence of hardware or a combination of hardware and software which is operable to perform the associated functions. Different elements of a computer, such as processor and/or memory, can be local, or in part or in whole remote and/or distributed and/or virtual.

A more detailed flowchart of an example authentication-related embodiment 600 is presented in FIG. 9.

Indeed, in such an embodiment, a process of authentication 600 can be divided in three main phases: acquisition, feature extraction and storage and, finally, the authentication of the individual itself. In the acquisition phase the chosen anatomical features of the individual are measured or recorded with a set of sensors. In the second phase, a set of features is extracted from the obtained data set to form a biometric key (response template data) and is stored in a secure database registered to the identified individual (individual A). In the authentication phase, an individual (individual B) is presenting himself as individual A, the chosen anatomical features of individual B are measured and compared to the biometric key A. Authentication occurs when there is correspondence between the two set of features.

For effectiveness, the following wants may exist for biometric keys:

Universality—applicable to all human beings.
Unicity—different from people to people.
Permanence—consistency over time.
Measurability—features set can be obtained and quantified in a timely fashion.
Accessibility—features set extraction are not cumbersome nor invasive for the user.
Remote contactless measurements.
Circumvention—difficulty to copy or counterfeit. (The level of difficulty is usually associated with the level of security required for a given application.)

One form of biometric authentication is based on facial recognition, such as via the inclusion of photographs in identification papers. Since then, facial recognition has evolved using parametrization of facial features allowing advanced algorithms to match those features with visible or NIR (near infrared) 2D images. Such systems have proven to be vulnerable to biometric replica such as a mask or a photograph. Complexity may be added by using a 3D camera, mask still being a method of counterfeiting.

Nowadays, fingerprints biometrics is integrated in most consumer electronics devices. It is mainly based on optical, capacitive or ultrasonic sensors. Palm prints may also be used as well as veinous structures in the hand or fingers. Veinous structures are revealed using polarized NIR imaging or photoacoustic tomography. People have also proposed IR imagery.

Iris recognition may also be used. High-resolution imaging can resolve unique patterns and color of the iris. Less vulnerable to reflections and environmental noise, NIR cameras are often preferred to visible camera systems. Still iris recognition is facing some measurability challenges due to eye blinking, eyelashes and eyelid occlusions and the possible presence of glasses and contact lenses.

For dynamical behavior biometrics, most common modalities include signature dynamics, heartbeat, voice, and gait. While gait analysis involves the use of cameras and signature dynamics needs inertial sensors, heartbeat and voice rely on acoustical or electrical measurements, even though heartbeat can be measured optically through blood circulation monitoring. In principle, these modalities should be more robust to counterfeiting since they require action/behavior from the individual to be identified. However, recording apparatus may circumvent these methodologies.

With advances in performances (sensitivity and accuracy) and lower cost of sensors, multimodality is becoming an affordable avenue to increase the complexity of counterfeiting, but often at the expense of measurability and/or accessibility. In all cases, anatomical features must be measured in a convenient fashion, likely resulting in the possibility to make those measurements covertly to fabricate faked replicas.

Brainwaves have been used for authentication, mainly using EEG and Event Related Potential (ERP) measurements. The subject is submitted to a stimuli sequence and the resulting brainwaves response is recorded. Some versions include a task to perform and either the alteration of the task by the stimuli sequence or the task itself is used for authentication. For example, one may look at modifications of typing micro-behaviors induced by the stimuli sequence or the brain response to a task such as identifying an object in a sequence of random images, the object being the secret code of the individual to be authenticated. Changes in the brain responses have also been used to detect impairment.

Various autonomic physiological parameters have been used to assist mental/neurological healthcare professionals during evaluation and treatment, to bring quantitative and longitudinal data in the process. Autonomic physiological parameters were used either during discussion/questioning with healthcare professionals or before/during/after a stimuli sequence. In some cases, the time interval between the stimuli and the cognitive response was used as a discriminant parameter. The stimuli sequence used was established to identify and follow the evolution of sensory and cognitive profiling. Artificial intelligence can be used to match a set of autonomic physiological parameters to a sensory and cognitive profile status.

In an embodiment, reflex responses to a stimuli sequence can be harnessed. The stimuli sequence being specific to each individual, involving personal, intimate memories and evoking specific and personal emotive response. Besides EEG, several techniques can be used to monitor emotive state or response, among them, face micro-expressions, voice tone, bodily movements, heartbeat variations and eye/iris movements.

Upon declaration of identity, an individual is submitted to a specific sequence of stimulations and the reflex responses are measured and compared to the previously recorded responses (key). To overcome the variability of the response from a single individual due to mood and/or health status, the stimuli sequence is a mix of personal and generic stimulations, the generic stimulations serving as a baseline over which the personal stimuli are superimposed and provide the biometric authentication. A Pass/Fail signal (or likelihood of confidence) is then provided on the result of the comparison. The stimuli sequence referring to personal experience is increasing the robustness of the key.

The stimuli sequence may be an audio-visual sequence and the monitored responses may be face micro expressions. To avoid circumvention, it is important that the stimuli sequences be sufficiently rapid to prevent from cognitive process to be present in the authentication process. It should also include personal and intimate experience references, resulting in specific emotive responses. In such situation, the key cannot be communicated since the individual doesn't know it himself. Should it be compromised (stolen database, for example), the stimuli sequence might be changed and a new personal key generated. The proposed authentication process is much more robust to counterfeit and offer re-initialization possibility which is not possible in current biometric authentication methods.

The same methodology can be used for mental/neurological health or alertness assessment. By measuring the reflex emotive response to a stimuli sequence including specific personal elements, the healthcare professional or the individual will have quantitative data about the reflex emotive status of the individual including intimate emotions not necessarily revealed during consultation or even known/realized by the individual. By comparing with the response to the same stimuli sequence provided at a slower pace allowing the cognitive process to take place, it is also possible to evaluate how the individual is managing such emotional states.

As can be understood, the examples described above and illustrated are intended to be exemplary only. Indeed, although the examples presented above present a stimuli sequence which includes both personal and generic images and which stimulates an actual physiological reflex response in a human, it will be understood that depending on the embodiment, the stimuli sequence can involve additional stimuli as well, such as stimuli which stimulate cognitive responses in addition to reflex responses, audible stimuli, touch-based stimuli, etc. The monitoring of the human exposed to the stimuli can be adapted accordingly, such as to produce response data which includes cognitive response elements in addition to reflex response elements for instance. The scope is indicated by the appended claims.

What is claimed is:

1. A computer-implemented method comprising:
   acquiring a user ID;
   acquiring response data including a digital representation of an actual physiological reflex response of a human to exposure to a stimuli sequence associated to the user ID, the stimuli sequence including a sequence of images, the images including personal images and generic images, the personal images being personal to the user ID, the response data including response data associated to the personal images and response data associated to the generic images;
   providing response template data associated to the user ID, the response template data including a digital representation of a baseline physiological reflex response of a user corresponding to the user ID to exposure to the stimuli sequence, the response template data including response template data associated to the personal images and response template data associated to the generic images;
   computing a normalization parameter based on a comparison between the response data associated to the generic images and the response template data associated to the generic images;
   comparing the response data associated to the personal images to the response template data associated to the personal images, including normalizing the response data associated to the personal images to the response template data associated to the personal images based on the normalization parameter; and
   generating an output based on said comparing the response data associated to the personal images.

2. The computer-implemented method of claim 1 wherein the generating the output includes authenticating the human as the user when the response data associated to the personal images matches the response template data associated to the personal images following the normalizing.

3. The computer-implemented method of claim 1 wherein acquiring the user ID includes receiving the user ID from a requester, and wherein the generating the output includes advising the requester of a result of the comparing the response data associated to the personal images.

4. The computer-implemented method of claim 3 wherein the results of the comparing are indicative of a physiological state.

5. The computer-implemented method of claim 1 wherein said providing response template data includes exposing the human to the stimuli sequence while monitoring the physiological reflex response of the human to the stimuli sequence.

6. The computer-implemented method of claim 1 wherein the response data has response timeslots, and the response template data has response template timeslots, the response timeslots being associated to exposure to respective ones of the personal images and the generic images of the stimuli sequence in a first order of images, the response template timeslots being associated to exposure to respective ones of the personal images and the generic images of the stimuli sequence in a second order of images, the second order of images being different than the first order of images.

7. The computer-implemented method of claim 1 wherein the response data has response timeslots, and the response template data has response template timeslots, the response timeslots being associated to exposure to respective ones of the personal images and the generic images of the stimuli sequence in a first order of images, the response template timeslots being associated to exposure to respective ones of the personal images and the generic images of the stimuli sequence in a second order of images, the second order of images being the same as the first order of images.

* * * * *